United States Patent [19]

Boggs

[11] Patent Number: 5,016,660
[45] Date of Patent: May 21, 1991

[54] AUTOMATIC FLOSSING TOOL

[76] Inventor: Michael S. Boggs, 106 N. Bryan St., Hicksville, Ohio 43526

[21] Appl. No.: 497,918

[22] Filed: Mar. 23, 1990

[51] Int. Cl.⁵ .............................................. A61C 15/00
[52] U.S. Cl. ..................................... 132/322; 132/323
[58] Field of Search ............... 132/322, 323, 324, 325, 132/326, 327

[56] References Cited

U.S. PATENT DOCUMENTS

| | | | |
|---|---|---|---|
| 3,759,274 | 9/1973 | Warner | 132/325 |
| 4,235,253 | 11/1980 | Moore | 132/322 |
| 4,307,740 | 12/1981 | Florindez et al. | 132/322 |
| 4,326,549 | 4/1982 | Hinding | 132/322 |
| 4,338,957 | 7/1982 | Meibauer | 132/322 |
| 4,458,702 | 7/1984 | Grollimund | 132/322 |
| 4,605,025 | 8/1986 | McSpadden | 132/322 |
| 4,706,695 | 11/1987 | Urso | 132/322 |

Primary Examiner—Gene Mancene
Assistant Examiner—Michael Lynch
Attorney, Agent, or Firm—Robert M. Sperry

[57] ABSTRACT

An improved dental flossing tool having reciprocating tines supporting the flossing material and biased apart to assure proper tension on the flossing material, while having means carried by the tines for moving the flossing material between the tines and having removable head means to permit replacement of the head to provide sterile use for subsequent users.

12 Claims, 2 Drawing Sheets

AUTOMATIC FLOSSING TOOL

BACKGROUND

1. Field of Invention

This invention relates to dental flossing tools and is especially directed to power driven flossing tools.

2. PRIOR ART

It is common knowledge that flossing teeth a necessary part of dental hygiene. Nevertheless, flossing is widely ignored by individuals. Many people find it difficult or unpleasant to reach into their mouths, as is necessary in order to cause the floss material to pass between the teeth. Other people are uncertain as to the proper motion to use to accomplish flossing. To overcome these problems, numerous devices have been proposed for facilitating the flossing operation. Unfortunately, many of the prior art flossing tools have been cumbersome and bulky and have been difficult for a patient to use. Other prior art flossing tools have simply held the flossing material in position, but have done nothing to facilitate proper movement of the flossing material. Furthermore, none of the prior art flossing tools is suitable for use by multiple patients. That is, the prior art flossing tools must either be used by only one person or must be sterilized between uses to prevent possible transfer of germs from one user to another. A search in the United States Patent Office has revealed the following:

| U.S. PAT. NO. | INVENTOR | ISSUED |
|---|---|---|
| 3,534,745 | W. A. Waters | Oct. 20, 1970 |
| 3,667,483 | J. B. McCabe | June 6, 1972 |
| 3,421,524 | W. A. Waters | Jan. 14, 1969 |
| 3,759,274 | C. E. Warner | Sep. 18, 1973 |
| 4,014,354 | T. H. Garrett | Mar. 29, 1977 |
| 4,235,253 | D. A. Moore | Nov. 25, 1980 |
| 3,847,167 | J. J. Brien | Nov. 12, 1974 |
| 4,245,658 | J. M. Lecouturier | Jan. 20, 1981 |
| 4,265,257 | J. R. Salyer | May 5, 1981 |
| 4,338,957 | R. H, Melbauer | July 13, 1982 |
| 4,458,702 | E. C. Grollimund | July 10, 1984 |
| 4,586,521 | C. L. Urso | May 6, 1986 |
| 4,605,025 | J. T. McSpadden | Aug. 12, 1986 |
| 4,830,032 | P. J. Jousson | May 16, 1989 |
| 4,307,740 | A. Florindez et al | Dec. 29, 1981 |

Unfortunately, each of these prior art flossing tools is subject to the objections noted above. Thus, none of the prior art flossing tools have been entirely satisfactory.

BRIEF SUMMARY AND OBJECTS OF INVENTION

These disadvantages of the prior art are overcome with the present invention and an improved dental flossing tool is provided which is simple and convenient to use and which is power operated to ensure proper movement of the flossing material, yet the flossing tool of the present invention may be provided with replaceable heads to permit sterile use by multiple users, if necessary.

These advantages of the present invention are preferably attained by providing an improved dental flossing tool having reciprocating tines supporting the flossing material and biased apart to assure proper tension on the flossing material, while having means carried by the tines for moving the flossing material between the tines and having removable head means to permit replacement of the head to provide sterile use for subsequent users.

Accordingly, it is an object of the present invention to provide an improved dental flossing tool.

Another object of the present invention is to provide an improved dental flossing tool having reciprocating tines for supporting the flossing material and assuring proper movement of the flossing material.

A further object of the present invention is to provide an improved dental flossing tool having reciprocating tines for supporting the flossing material and assuring proper movement of the flossing material and means biasing the tines apart to maintain proper tension on the flossing material.

An additional object of the present invention is to provide an improved dental flossing tool having reciprocating tines for supporting the flossing material and assuring proper movement of the flossing material and means biasing the tines apart to maintain proper tension on the flossing material and having means carried by the tines for moving the flossing material between the tines to further assure proper movement of the flossing material.

An additional object of the present invention is to provide an improved dental flossing tool having removable head means to permit replacement of the head to provide sterile use for subsequent users.

A specific object of the present invention is to provide an improved dental flossing tool having reciprocating tines supporting the flossing material and biased apart to assure proper tension on the flossing material, while having means carried by the tines for moving the flossing material between the tines and having removable head means to permit replacement of the head to provide sterile use for subsequent users.

These and other objects and features of the present invention will be apparent from the following detailed description, taken with reference to the figures of the accompanying drawings.

DETAILED DESCRIPTION OF THE INVENTION

Figures 1, 2:
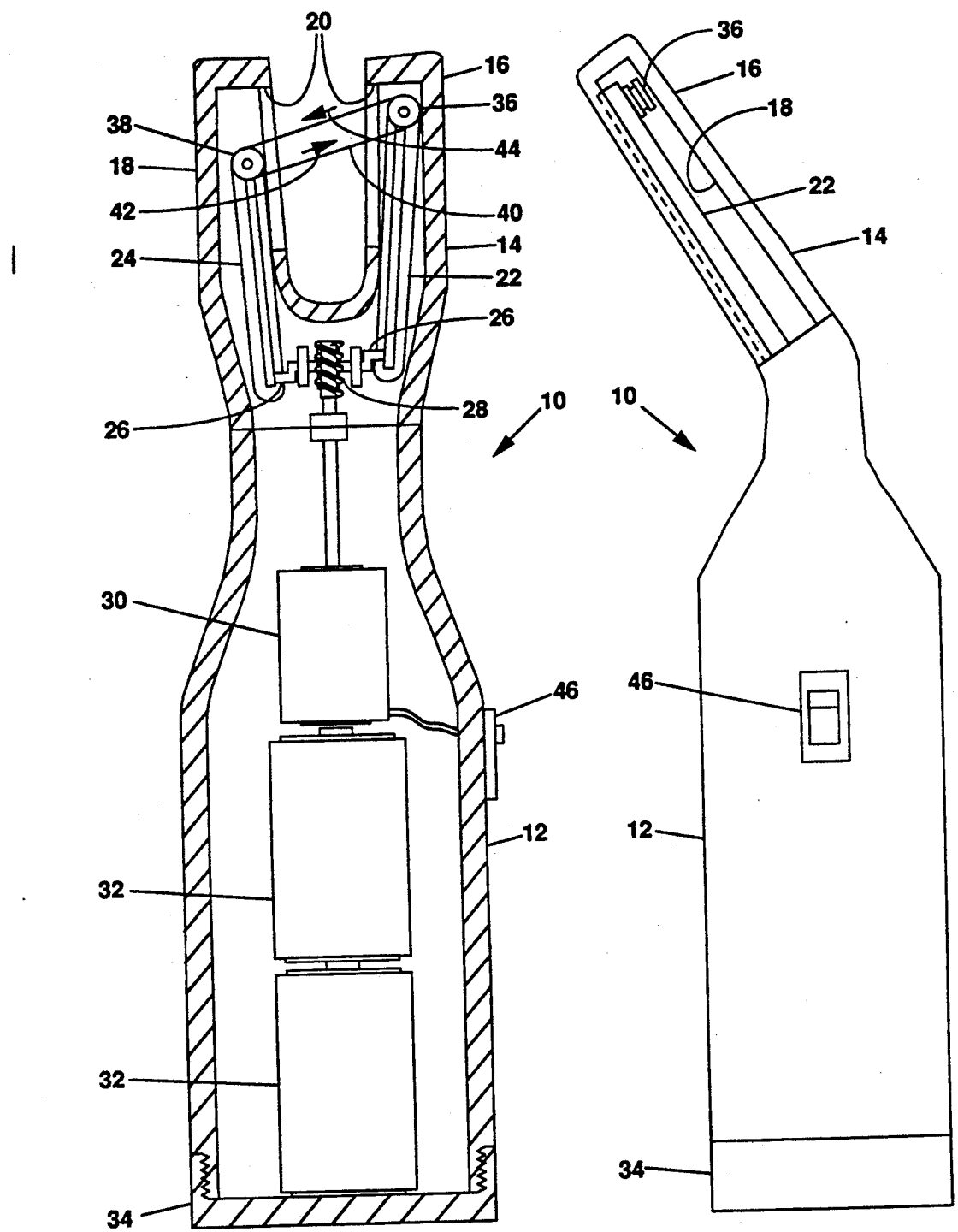
FIG. 1 is a vertical section through a dental flossing tool embodying the present invention.
FIG. 2 is a side elevation of the dental flossing tool of FIG. 1, shown with one of the tines broken away for clarity.

In that form of the present invention chosen for purposes of illustration in FIGS. 1 and 2, a dental flossing tool, indicated generally at 10, is shown comprising an elongated, hollow handle portion 12 with a bifurcated head portion 14 mounted on the upper end of the handle 12 and having a pair of generally parallel arms 16 and 18 extending at an angle of approximately 60° to the axis of the handle 12 and formed with slots 20 formed on the facing sides of each of the arms 16 and 18. Within each of the arms 16 and 18 are a pair of tines 22 and 24 which are capable of reciprocal movement within the respective arms 16 and 18 by means of a crank 26 which is driven through suitable gearing 28 by a motor 30. As seen in FIG. 1, the motor 30 is powered by suitable batteries 32 which are located within the handle 12 and are replaceable by removing the lower end 34 of the handle 12. A pair of drive wheels 36 and 38 are mounted adjacent the outer ends of each of the tines 22 and 24 and a loop of dental flossing material is positioned about the drive wheels 36 and 38 in a FIG. 8 configuration, as seen at 40 in FIG. 1. The wheels 36 and 38 are rotated by suitable drive means located within the tines 22 and 24, such as the drive means shown in FIG. 5, and serve to move the flossing material between the tines 22 and 24, as indicated by arrows 42 and 44 in FIG. 1. The motor 30 is controlled by means of a switch 46 mounted on the side of the handle 12 and activate both the reciprocal movement of the tines 22 and 24 and the rotation of the drive wheels 36 and 38.

In use, the user places a loop of dental flossing material 40 about the drive wheels 36 and 38 through the slots 20 of the arms 16 and 18 of the head portion 14. Thereafter, the user activates the dental flossing tool 10 by moving the switch 46 to the "ON" position. This causes the motor 30 to operate the gearing 28 to rotate the crank 26 which serves to alternately move the tines 22 and 24 in a reciprocal path within the arms 16 and 18. At the same time, the motor 30 serves to rotate the drive wheels 36 and 38 adjacent the outer ends of the tines 22 and 24 which causes the flossing material 40 to move in a figure 8 path between the tines 22 and 24, as indicated by arrows 42 and 44 in FIG. 1. The user simply places the head 14 of the dental flossing tool 10 within their mouth in a position such that one arm 16 or 18 of the tool 10 is located behind their teeth, while the other arm 18 or 16 of the tool is located outside the teeth and guides the flossing material into the space between adjacent teeth. As this is done, the reciprocal movement of the tines 22 and 24 coupled with the movement of the flossing material 40 between the tines 22 and 24, under the action of drive wheels 36 and 38 assures proper movement of the flossing material 40 to accomplish thorough and effective flossing of the user's teeth.

Figure 3:
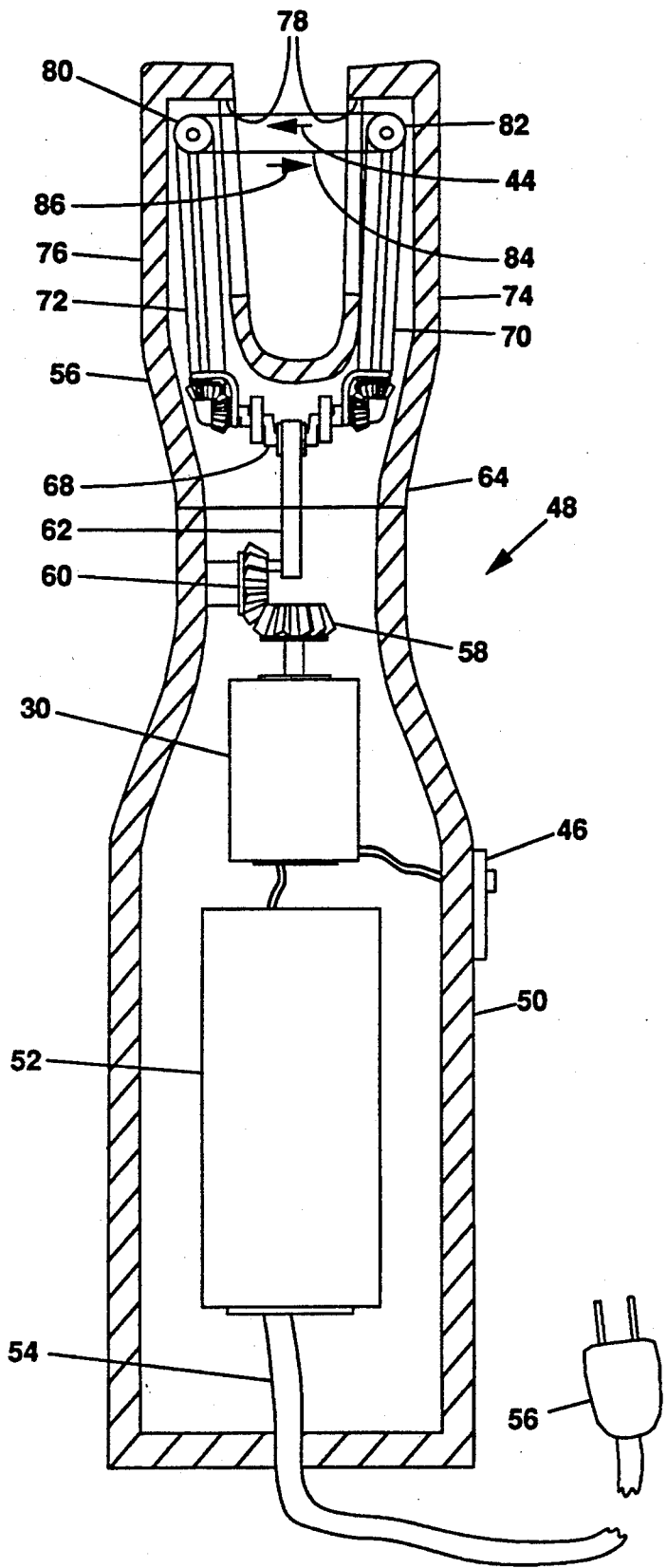
FIG. 3 is a view, similar to that of FIG. 1, showing an alternative form of the dental flossing tool of FIG. 1.

FIG. 3 shows an alternative form of the dental flossing tool 10 of FIG. 1. In this form of the invention, a dental flossing tool, indicated generally at 48, is shown having a hollow, generally cylindrical handle portion 50 containing a motor 52 provided with an electrical cord 54 having a plug 56 which is insertable into a standard electrical outlet, not shown, to provide power for the motor 52. In this form of the present invention, the bifurcated head portion 56 is removable and the motor 52 drives suitable gearing 58 which rotate a bevel gear 60. The head portion 56 has a shaft 62 which projects out of the lower end 64 of the head portion 56. A gear 66 is mounted on the outer end of the shaft 62 and is releasably engageable with the bevel gear 60 in the handle portion 50 for rotation by the motor 52. The gear 66 serves to drive a crank 68 which, in turn, moves tines 70 and 72 in a reciprocal path within the arms 74 and 76 of the bifurcated head portion 56. In this form of the present invention, the arms 74 and 76 are formed with slots 78 on a common side and drive wheels 80 and 82 are mounted adjacent the outer ends of the tines 70 and 72 in a manner such that the drive wheels 80 and 82 project out of the slots 78 to receive a loop of flossing material 84.

Figure 4:
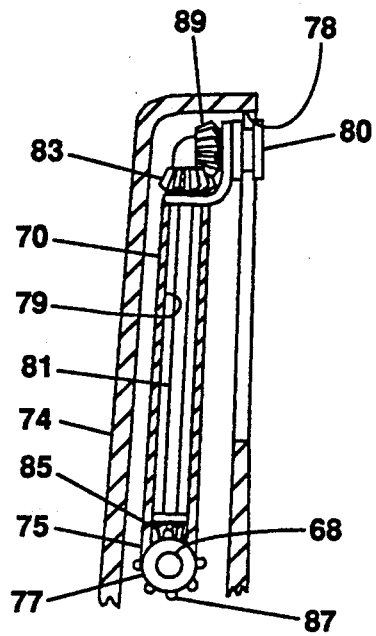
FIG. 4 is an enlarged detail view showing the gearing for driving one of the drive wheels of the dental flossing tool of FIG. 4.

As best seen in FIG. 4, the tines 70 and 72 are hollow cylinders having extensions 75 which encircle the adjacent end 77 of the crank 68 and have a central chamber 79 which houses a shaft 81 having gears 83 and 85 secured to the upper and lower ends, respectively, of the shaft 81. Also, end 77 of the crank 68 carries a gear 87 which engages and serves to drive gear 85 of shaft 81. This, in turn, rotates gear 83 which drives a gear 89 which is connected to drive wheel 80. Thus, as crank 68 rotates, gear 87 drives gear 83, shaft 81, gears 85 and 89 and, hence, rotates drive wheel 80, which serves to move the flossing material 84 between the tines 70 and 72, as indicated by arrow 86, in FIG. 3..

In use, the dental flossing tool 48 of FIG. 3 functions in substantially the same manner as the dental flossing tool 10 of FIG. 1. In other words, motor 52 drives the gearing 58 to rotate bevel gear 60, which rotates gear 66 on the end of shaft 62 to rotate crank 68 and, hence, to cause the tines 70 and 72 to move in a reciprocal manner within the arms 74 and 76 of the head portion 56. At the same time, the drive wheels 80 and 82 rotate to move the flossing material 84 between the tines 70 and 72. When one user has finished the flossing operation, the head portion 56 of the dental flossing tool 48 is removed and may be sterilized or discarded, while another head portion 56 is mounted on the handle portion 50 to enable a subsequent user to perform the flossing operation with a sterile head portion 56. This permits each user to have a sterile head portion 56 and prevents the possibility of germs being transferred from one user to another.

Figure 5:
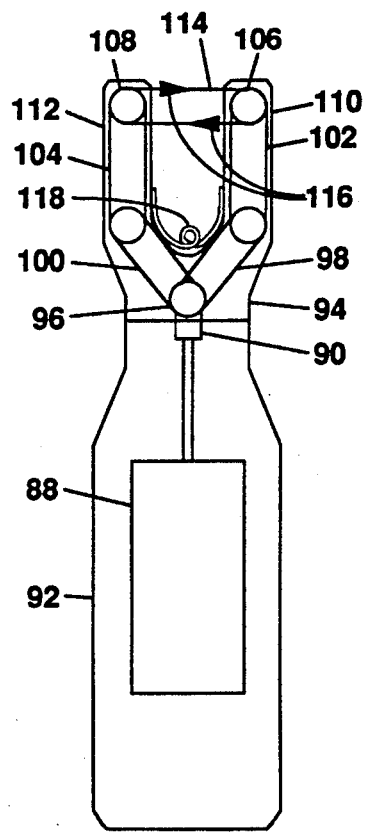
FIG. 5 is a view, similar to that of FIG. 1, showing a further alternative form of the dental flossing tool of FIG. 1.

FIG. 5 shows a further alternative form of the dental flossing tool of the present invention. In this form of the present invention, the motor 88 drives a friction clutch member 90 within the handle portion 92 of the dental flossing tool 94, while the removable head portion 94 contains a clutch engaging member 96 which is rotatable by the clutch member 90 and serves to drive a series of belts 98, 100, 102 and 104 to rotate drive wheels 106 and 108 located adjacent the outer ends of arms 110 and 112 of the disposable head portion 94. A loop of dental flossing material 114 is positioned on the drive wheels 106 and 108 and is caused by the drive wheels 106 and 108 to move between the arms 110 and 112, as indicated by arrow 116. In addition, resilient means, such as spring 118, serves to urge the arms 110 and 112 apart to assure that proper tension is provided for the loop of flossing material 114. When one user has completed the flossing operation, the head portion 94 may be replaced by a sterile head portion 94 for use by a subsequent user.

Obviously, numerous variations and modifications can be made without departing form the spirit of the present invention. Therefore, it should be clearly understood that the forms of the present invention described above and shown in the figures of the accompanying drawing are illustrative only and are not intended to limit the scope of the present invention.

I claim:

1. A dental flossing tool comprising:
a hollow, generally cylindrical handle,
a bifurcated head portion mounted on one end of said handle and having a pair of arms extending upwardly from said handle,
means carried by the arms of said head portion and movable within said arms for supporting a quantity of dental flossing material,
a motor located within said handle, and
drive means coupling said motor to move the flossing material supporting means to provide movement to said flossing material in a direction substantially parallel to the longitudinal axis of said tools.

2. The dental flossing tool of claim 1 wherein:
the arms of said head portion extend at an angle of approximately 60° to the axis of said handle.

3. The dental flossing tool of claim 1 wherein:
said drive means includes a pair of tines each moveable within a respective one of said arms and each carrying said floss supporting means, and
a crank driven by said motor for causing reciprocal movement of said tines to move said floss supporting means.

4. The dental flossing tool of claim 3 wherein:
said crank serves to cause alternate reciprocating movement of said tines.

5. The dental flossing tool of claim 3 wherein:
said crank serves to cause simultaneous reciprocating movement of said tines.

6. The dental flossing tool of claim 3 wherein: said floss supporting means are wheels and said crank serves to cause reciprocal movement of said tines and also to cause rotation of said wheels.

7. The dental flossing tool of claim 1 wherein: said floss supporting means are wheels.

8. The dental flossing tool of claim 7 wherein:
said wheels are driven by said drive means.

9. The dental flossing tool of claim 1 wherein:
said head portion is removably mounted on said handle.

10. The dental flossing tool of claim 1 further comprising:
resilient means normally urging said arms apart to assure proper tension on said flossing material.

11. The dental flossing tool of claim 1 wherein:
said drive means includes a clutch member, and
means driveable by said clutch for moving said floss supporting means.

12. The dental flossing tool of claim 1 wherein:
said head portion is removably mounted on said handle and said means driveable by said clutch is located within said head portion, while said clutch is located within said handle.

* * * * *